(12) United States Patent
Chan et al.

(10) Patent No.: US 7,226,733 B2
(45) Date of Patent: Jun. 5, 2007

(54) MICROCAVITY BIOSENSOR AND USES THEREOF

(75) Inventors: Selena Chan, Sunnyvale, CA (US); Philippe M. Fauchet, Pittsford, NY (US); Scott R. Horner, Rochester, NY (US); Benjamin L. Miller, Rochester, NY (US)

(73) Assignee: University of Rochester, Rochester, NY (US)

( * ) Notice: Subject to any disclaimer, the term of this patent is extended or adjusted under 35 U.S.C. 154(b) by 270 days.

(21) Appl. No.: 10/082,634

(22) Filed: Feb. 21, 2002

(65) Prior Publication Data

US 2002/0192680 A1 Dec. 19, 2002

Related U.S. Application Data

(60) Provisional application No. 60/270,527, filed on Feb. 21, 2001.

(51) Int. Cl.
*C12Q 1/68* (2006.01)
*C12M 1/00* (2006.01)
*G01N 16/06* (2006.01)
*C07H 21/04* (2006.01)

(52) U.S. Cl. ............................ 435/6; 435/7.1; 435/174; 435/283.1; 435/287.8; 435/288.7; 422/68.1; 422/82.05; 536/23.1; 536/24.3; 530/300; 530/350

(58) Field of Classification Search .................... 435/6, 435/7.1, 174, 283.1, 287.8, 288.7; 422/68.1, 422/82.05; 536/23.1, 24.3; 530/300, 350
See application file for complete search history.

(56) References Cited

U.S. PATENT DOCUMENTS 5,023,200 A    6/1991  Blewer et al.
5,550,063 A    8/1996  Bogart
5,629,214 A    5/1997  Crosby
6,248,539 B1   6/2001  Ghadiri et al.
6,770,480 B1   8/2004  Canham

FOREIGN PATENT DOCUMENTS

WO    WO 97/06101       2/1997
WO    WO 03/015636 A1   2/2003

OTHER PUBLICATIONS

Chan et al., "Porous Silicon Microcavities for Biosensing Applications," *Physica Status Solidi A* 182:541–546 (2000).
Chan et al., "Nanoscale Silicon Microcavity Optical Sensors for Biological Applications," Material Research Society Proceedings Symposium F (vol. 638) F.10.4 (2000).
Chan et al., "Identification of Gram Negative Bacteria Using Nanoscale Silicon Microcavities," *J. Am. Chem. Soc.* 123(47):11797–11798 (2001).
Chan et al., "Tunable, Narrow, and Directional Luminescence From Porous Silicon Light Emitting Devices," *Applied Physics Letters* 75(2):274–276 (1999).
Chan et al., "Nanoscale Microcavities for Biomedical Sensor Applications," In Micro– and Nanotechnology for Biomedical and Environmental Applications, Proceedings of SPIE, 3912:23–34 (2000).

(Continued)

*Primary Examiner*—Bj Forman
(74) *Attorney, Agent, or Firm*—Nixon Peabody LLP

(57) ABSTRACT

A biological sensor which includes: a porous semiconductor structure comprising a central layer interposed between upper and lower layers, each of the upper and lower layers including strata of alternating porosity; and one or more probes coupled to the porous semiconductor structure, the one or more probes binding to a target molecule, whereby a detectable change occurs in a refractive index of the biological sensor upon binding of the one or more probes to the target molecule. Methods of making the biological sensor and methods of using the same are disclosed, as is a detection device which includes such a biological sensor.

34 Claims, 11 Drawing Sheets

OTHER PUBLICATIONS

Chan et al., "Silicon Interference Filters and Bragg Reflectors for Active and Passive Integrated Optoelectronic Components," SPEI Conference on Silicon–Based Optoelectronics, San Jose, California, 3630:144–154 (1999).

Chan et al., "Porous Silicon Multilayer Mirrors and Microactivity Resonators for Optoelectronic Applications," Material Research Society Proceedings Symposium, 536:117–122 (1999).

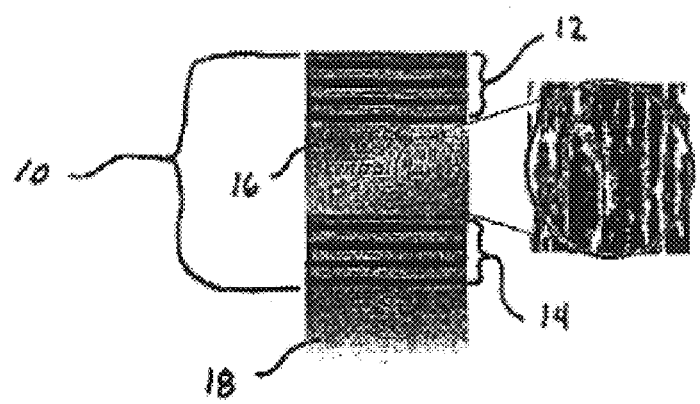
Figure 1
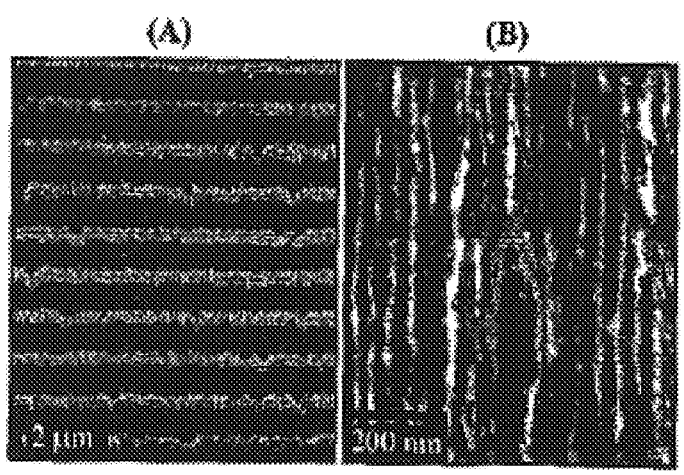
Figure 2A-B

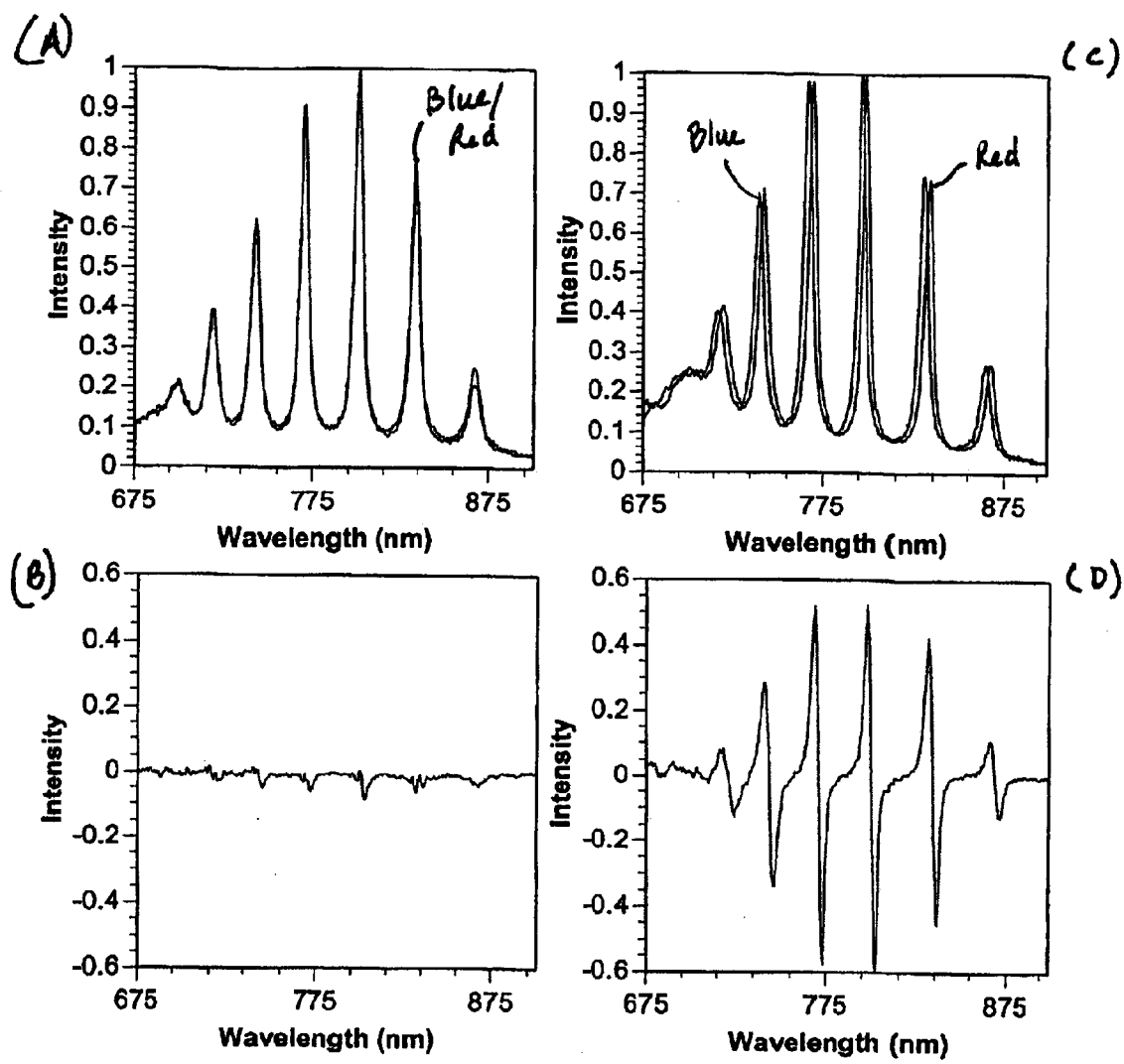
Figures 8A-D

SEQUENCE LISTING

```
<160> NUMBER OF SEQ ID NOS: 3

<210> SEQ ID NO 1
<211> LENGTH: 24
<212> TYPE: DNA
<213> ORGANISM: Artificial Sequence
<220> FEATURE:
<223> OTHER INFORMATION: Description of Artificial Sequence:
      oligonucleotide probe

<400> SEQUENCE: 1
tagctatgga attcctcgta ggca                                          24

<210> SEQ ID NO 2
<211> LENGTH: 22
<212> TYPE: DNA
<213> ORGANISM: Artificial Sequence
<220> FEATURE:
<223> OTHER INFORMATION: Description of Artificial Sequence:
      oligonucleotide target

<400> SEQUENCE: 2
gcctacgagg aattccatag ct                                            22

<210> SEQ ID NO 3
<211> LENGTH: 30
<212> TYPE: DNA
```

-continued

```
<213> ORGANISM: Artificial Sequence
<220> FEATURE:
<223> OTHER INFORMATION: Description of Artificial Sequence:
      oligonucleotide probe for bacteriophage lambda DNA

<400> SEQUENCE: 3
tcggagagcc ttcctgttca atatcatcat                                              30
```

MICROCAVITY BIOSENSOR AND USES THEREOF

This application claims the benefit of U.S. Provisional Patent Application Serial No. 60/270,527 filed Feb. 21, 2001, which is hereby incorporated by reference in its entirety.

The present invention was made, at least in part, with funding received from the U.S. Army Research Office, grant numbers 5-28888 and 5-27987. The U.S. government may have certain rights in this invention.

FIELD OF THE INVENTION

This invention relates to microcavity biosensors which are useful for identifying the presence of a biological target molecule or organism in a sample, as well as methods of making such microcavity biosensors and their use.

BACKGROUND OF THE INVENTION

Ever increasing attention is being paid to detection and analysis of low concentrations of analytes in various biologic and organic environments. Qualitative analysis of such analytes is generally limited to the higher concentration levels, whereas quantitative analysis usually requires labeling with a radioisotope or fluorescent reagent. Such procedures are time consuming and inconvenient. Thus, it would be extremely beneficial to have a quick and simple means of qualitatively and quantitatively detecting analytes at low concentration levels.

Solid-state sensors and particularly biosensors have received considerable attention lately due to their increasing utility in chemical, biological, and pharmaceutical research as well as disease diagnostics. In general, biosensors consist of two components: a highly specific recognition element and a transducing structure that converts the molecular recognition event into a quantifiable signal. Biosensors have been developed to detect a variety of biomolecular complexes including oligonucleotide pairs, antibody-antigen, hormone-receptor, enzyme-substrate and lectin-glycoprotein interactions. Signal transductions are generally accomplished with electrochemical, field-effect transistor, optical absorption, fluorescence or interferometric devices.

It is known that the intensity of the visible reflectivity changes of a porous silicon film can be utilized in a simple biological sensor, as disclosed in U.S. Pat. No. 6,248,539 to Ghadiri et al. As disclosed therein, the detection and measurement of the wavelength shifts in the interference spectra of a porous semiconductor substrate such as a silicon substrate make possible the detection, identification and quantification of small molecules. While such a biological sensor is certainly useful, its sensitivity is lacking in that detection of a reflectivity shift is complicated by a broad peak rather than one or more sharply defined luminescent peaks.

The present invention is directed to overcoming these and other deficiencies in the art.

SUMMARY OF THE INVENTION

One aspect of the present invention relates to a biological sensor which includes: a porous semiconductor structure comprising a central layer interposed between upper and lower layers, each of the upper and lower layers including strata of alternating porosity; and one or more probes coupled to the porous semiconductor structure, the one or more probes binding to a target molecule, whereby a detectable change occurs in a refractive index of the biological sensor upon binding of the one or more probes to the target molecule.

A second aspect of the present invention relates to a detection device which includes: a biological sensor of the present invention; a source of illumination positioned to illuminate the biological sensor; and a detector positioned to capture photoluminescent emissions from the biological sensor and to detect changes in photoluminescent emissions from the biological sensor.

A third aspect of the present invention relates to a method of making a biological sensor which detects a target molecule. This method includes: providing a primed porous semiconductor structure including a central layer interposed between upper and lower layers, each of the upper and lower layers including strata of alternating porosity, and a coupling agent bound to the semiconductor structure; and exposing the primed porous semiconductor structure to a probe molecule including (i) one or more semiconductor structure-binding groups and (ii) one or more target-binding groups that bind to a target molecule, said exposing being carried out under conditions effective to bind the probe molecule to the primed porous semiconductor structure via the coupling agent or directly to the semiconductor structure upon displacement of the coupling agent, with the one or more target-binding groups remaining available for binding to the target molecule.

A fourth aspect of the present invention relates to a method of detecting a target molecule which includes: exposing a biological sensor of the present invention to a sample under conditions effective to allow binding of a target molecule in the sample to the one or more probes of the biological sensor; and determining whether the biological sensor emits a photoluminescent emission pattern which shifts following said exposing, whereby a shifted photoluminescent emission pattern indicates the presence of the target molecule in the sample.

A fifth aspect of the present invention relates to a method of detecting the presence of Gram negative bacteria in a sample which includes: exposing a sample to a biological sensor comprising (i) a porous photoluminescent semiconductor structure comprising a central layer interposed between upper and lower layers, each upper and lower layer including strata of alternating porosity and (ii) one or more probes coupled to the porous photoluminescent semiconductor structure, the one or more probes binding to lipid A or fragments thereof; and determining whether the biological sensor emits a photoluminescent emission pattern which shifts following said exposing, whereby a shifted photoluminescent emission pattern indicates the presence of lipid A and, thus, Gram negative bacteria in the sample.

A structure as described above, containing a central layer (microcavity) between upper and lower layers (Bragg reflectors), forms a microcavity resonator. This microcavity resonator solves several problems of other biological sensors using a simple porous silicon substrate (i.e., without the Bragg reflectors), one such problem being the presence of a broad photoluminescent peak. The microcavity resonator affords greater sensitivity in sensing the presence of biological targets. By confining the luminescence generated in the central layer of the microcavity by two Bragg reflectors, the photoluminescence spectrum is composed of multiple sharp and narrow peaks with FWHM values of about 3 nm (Chan et al., *Phys. Stat. Sol. A* 182:541–546 (2000), which is hereby incorporated by reference in its entirety). Upon a refractive index change, the photoluminescent spikes shift, thereby generating a large, detectable differential signal.

BRIEF DESCRIPTION OF THE DRAWINGS

FIG. 1 illustrates schematically a porous silicon structure of the present invention, with the enlargement showing an electron micrograph image of the central layer. Etched pores within the central layer are clearly visible.

FIGS. 2A–B are cross sectional SEM micrographs of a microcavity porous silicon structure which is used to form a biosensor of the present invention. FIG. 2A is a cross-sectional SEM micrograph of a 10 period p+ oxidized porous silicon multilayer mirror with overall thickness of ~2.4 μm. The thickness of the low porosity layers (43%) is 80 nm and high porosity layers (62%) is 160 nm. FIG. 2B is a cross-sectional micrograph of a porous silicon microcavity active layer with 68% porosity. Pore sizes range from 50–75 nm.

FIG. 4B depicts schematically a "lock and key" binding of the DNA to its complementary DNA in the porous silicon sensor.

FIGS. 8A–D illustrate photoluminescence spectra of a porous silicon microcavity biosensor in the presence and absence of bacterial cell lysates. Blue spectra: sensor alone following derivatization with TWTCP and glycine methyl ester. Red spectra: sensor photoluminescence following incubation with cell lysates from Gram-(+) bacteria (*Bacillus subtilis*, 8A–B) or Gram-(–) bacteria (*Escherichia coli*, 8C–D). The spectra in FIGS. 8B, 8D are the difference between spectra obtained in the presence and absence of bacterial cell lysates (from FIGS. 8A, 8C, respectively).

DETAILED DESCRIPTION OF THE INVENTION

Figure 3A:
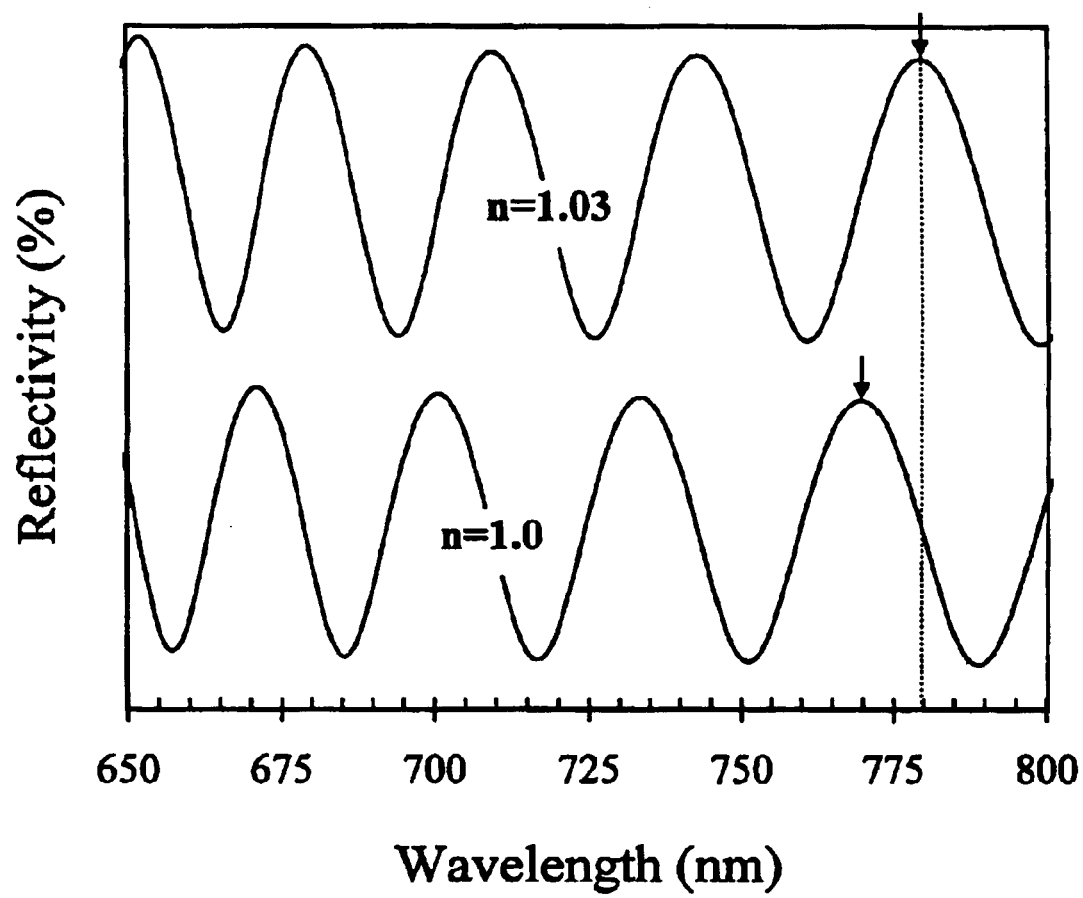
FIGS. 3A–B illustrate the reflectivity spectra of a single layer of porous silicon (3A) and the reflectivity spectra for a microcavity (3B). No "off-on" states are seen for the porous single layers, while in the microcavity case, a clear "off" state and "on" state are evident. The refractive index changes from n=1.0 to n=1.03.

One aspect of the present invention relates to a biological sensor which includes a porous semiconductor structure and one or more probes coupled to the porous semiconductor structure. The porous semiconductor structure can be formed onto any suitable substrate (e.g., on a chip, wafer, etc.).

The porous semiconductor structure includes a central layer (a microcavity) interposed between upper and lower layers, each of the upper and lower layers including strata of alternating porosity. The upper and lower layers form Bragg reflectors.

Semiconductors which can be used to form the porous semiconductor structure can be a single semiconductor material, a combination of semiconductor materials which are unmixed, or a mixture of semiconductor materials. The semiconductor is preferably one which is photoluminescent in its porous state. By virtue of the Bragg reflectors (i.e., the upper and lower layers), the emitted photoluminescence spectrum is composed of multiple sharp and narrow peaks. The light can be in the visible portion of the electromagnetic spectrum (i.e., 350–800 nm), the infrared region (i.e., 800–3000 nm), and the ultraviolet region (i.e., 50–350 nm). These wavelengths are only exemplary and can vary according to the type of semiconductor material(s) used to form the porous semiconductor structure, the thickness thereof, as well as the porosity thereof (including pore size).

Preferred semiconductors which can be used to form the porous semiconductor structure include, without limitation, silicon and silicon alloys. The semiconductor is amenable to galvanic etching processes which can be used to form the porous structure. These semiconductor materials can include p-doped silicon (e.g., $(CH_3)_2Zn$, $(C_2H_5)_2Zn$, $(C_2H_5)_2Be$, $(CH_3)_2Cd$, $(C_2H_5)_2Mg$, B, Al, Ga, In), n-doped (e.g., $H_2Se$, $H_2S$, $CH_3Sn$, $(C_2H_5)_3S$, $SiH_4$, $Si_2H_6$, P, As, Sb) silicon, intrinsic or undoped silicon, alloys of these materials with, for example, germanium in amounts of up to about 10% by weight, mixtures of these materials, and semiconductor materials based on Group III element nitrides.

Two primary advantages make porous silicon (or nanoscale silicon) an attractive material for biosensing applications. First, its enormous surface area ranges from about 90 m²/cm³ to about 783 m²/cm³ (Herino, "Pore Size Distribution in Porous Silicon" *In Properties of Porous Silicon*, Canham (ed.), The Institution of Electrical Engineers, London, United Kingdom, 89 (1997), which is hereby incorporated by reference in its entirety), which provides numerous sites for many potential species to attach (Lauerhaas et al., *Science* 261:1567–1568 (1993), which is hereby incorporated by reference in its entirety). Second, its eye-detectable, room temperature luminescence spans the visible spectrum (Canham, *Appl. Phys. Left.* 57:1046–1048 (1990), which is hereby incorporated by reference in its entirety), which makes it an effective transducer.

The porous semiconductor structure can range in thickness from about 1 to about 30 microns. Typically, the thickness will vary inversely according to the desired porosity (i.e., higher porosity structures will be thicker than lower porosity structures) as well as according to the wavelength of light to be detected (i.e., structures which are used with shorter wavelength light can be thinner than structures which are used with longer wavelength light).

The pores (or cavities) in the porous semiconductor structure are typically sized in terms of their nominal "diameter" notwithstanding the fact that they are somewhat irregular in shape and vary in diameter from one strata to another. These diameters range from about 2 nm to about 2000 nm, with diameters of about 10 to about 100 nm being preferred for visible light, about 2 to about 50 nm diameters being preferred for ultraviolet light, and 100 to 2000 nm being preferred for infrared light. The nominal pore diameter should also be selected based upon the size of the target molecule to be detected.

As noted above, the porosity of the structure, including its central layer, will vary inversely according to its thickness. Typically, the porosity of the central layer is about 50 to about 90 percent, although slightly lower or higher porosity may be attained for specific applications. For most applications, the porosity is preferably about 65 to about 85 percent.

The upper and lower layers individually contain strata of alternating porosity, i.e., higher and lower porosity strata, relative to the adjacent strata. The upper layer and lower layer can be symmetrical (i.e., having the same configuration, including the number of strata) or they can be different (i.e., having different strata configurations in number and/or porosity). Typically, the total number of strata is six or more (i.e., three or more high porosity strata and three or more low porosity strata in an alternating configuration).

The lower porosity strata simply have a porosity which is less than the porosity of their adjacent higher porosity strata. The lower porosity strata preferably have a porosity of about 35 to about 70 percent, more preferably about 40 to about 60 percent. The higher porosity strata preferably have a porosity of about 55 to about 80 percent, more preferably between about 60 to about 80 percent.

Within each of the upper and lower layers on opposite sides of the central layer, the low porosity and high porosity strata need not be the same throughout. Thus, different low porosity strata and different high porosity strata can be present within a single upper or lower layer. Alternatively, the low porosity strata and the high porosity strata will be substantially consistent within the upper and lower layers.

The porous semiconductor structure can be formed by electrochemical etching. For example, an etching solution is prepared by adding a volume of pure ethanol to an aqueous solution of HF, e.g., from about 15% to about 50% by weight HF. Basically, the semiconductor material is introduced into the etching solution and a platinum or other inert cathode is provided in solution. The etching cell is the exposed to an anodic current (Canham, *Appl. Phys. Lett.* 57:1046–1048 (1990); and Bsiesy et al., *Surface Science* 254:195–200 (1991), each of which is hereby incorporated by reference in its entirety). The anodic current densities can be selected by one of ordinary skill in the art according to the type of semiconductor material, the degree of porosity which is desired in the final porous structure, etc. Specifically, to create the Bragg reflectors the current is changed over a time course to afford a higher rate of etching (creating the high porosity strata) and a lower rate of etching (creating the low porosity strata).

After etching, the porous semiconductor structure is rinsed in ethanol and dried under a stream of inert gas ($N_2$) or an oxidative gas ($O_2$, $O_3$, or $Br_2$). Thereafter, the porous semiconductor structure can be hydrolyzed in air.

The resulting porous semiconductor structure 10 has a configuration as illustrated in FIG. 1, with the upper layer 12 and the lower layer 14 on opposite sides of the central layer 16 which is the microcavity. The porous semiconductor structure 10 is formed on a substrate 18 (e.g., c-Si). FIGS. 2A shows a cross-sectional SEM micrograph of a 10 period p+ oxidized porous silicon multilayer mirror (one of the Bragg reflectors) with overall thickness of ~2.4 µm. Within the upper and lower layers, the thickness of the low porosity strata (43%) is 80 nm and high porosity strata (62%) is 160 nm. FIG. 2B is a cross-sectional micrograph of a porous silicon microcavity (i.e., the central layer) with 68% porosity and pore sizes ranging from about 50 to about 75 nm.

To form a biological sensor from the porous semiconductor structure, one or more probes which bind to a target molecule are coupled to the porous semiconductor structure. The one or more probes each include (i) one or more semiconductor-binding groups which enable them to be coupled to the semiconductor structure (either directly or via a coupling agent) and (ii) one or more target-binding groups that bind to a target molecule. Although not limited to such, the one or more semiconductor-binding groups are typically hydroxyl groups. The one or more target-binding groups can include, without limitation, an amino group, a thiol, a hydroxyl, an alkyl chain, an ester, a carboxylic acid, an aromatic, a heterocycle, or a combination thereof.

Suitable probes generally include, without limitation, non-polymeric small molecules, polypeptides or proteins, and oligonucleotides.

Exemplary non-polymeric small molecules include, without limitation: avidin, peptido-mimetic compounds, and vancomycin. One class of peptido-mimetic compounds is disclosed in U.S. patent application Ser. No. 09/568,403 to Miller et al., filed May 10, 2000, each of which is hereby incorporated herein by reference in its entirety. A preferred peptido-mimetic compound which binds to lipopolysaccharide is a tetratryptophan ter-cyclopentane as disclosed in the above-noted application to Miller et al. Other peptidomimetic compounds can also be employed.

Exemplary polypeptides include, without limitation, a receptor for cell surface molecule or fragment thereof; a lipid A receptor; an antibody or fragment thereof; peptide monobodies of the type disclosed in U.S. patent application Ser. No. 09/096,749 to Koide, filed Jun. 12, 1998, and U.S. patent application Ser. No. 10/006,760 to Koide, filed Nov. 19, 2001, each of which is hereby incorporated by reference in its entirety; a lipopolysacchardide-binding polypeptide; a peptidoglycan-binding polypeptide; a carbohydrate-binding polypeptide; a phosphate-binding polypeptide; a nucleic acid-binding polypeptide; and polypeptides which bind organic warfare agents such as tabun, sarin, soman, GF, VX, mustard agents, botulinium toxin, Staphylococcus enterotoxin B, and saitotoxin.

Exemplary oligonucleotide probes can by DNA, RNA, or modified (e.g., propynylated) oligonucleotides of the type disclosed in Barnes et al., *J. Am. Chem. Soc.* 123:4107–4118 (2001), and Barnes et al., *J. Am. Chem. Soc.* 123:9186–9187 (2001), each of which is hereby incorporated by reference in its entirety. The oligonucleotide probes can be any length which is suitable to provide specificity for the intended target. Typically, oligonucleotide probes which do not contain modified nucleotides will be at least about 12 to about 100 nucleotides in length. For oligonucleotides which contain modified bases, oligonucleotides should be at least about 7 nucleotides in length, up to about 100 nucleotides in length.

Target molecules that can be bound be the one or more probes include, without limitation: proteins (including without limitation enzymes, antibodies or fragments thereof), glycoproteins, peptidoglycans, carbohydrates, lipoproteins, a lipoteichoic acid, lipid A, phosphates, nucleic acids which are expressed by certain pathogens (e.g., bacteria, viruses, multicellular fungi, yeasts, protozoans, multicellular parasites, etc.), or organic compounds such as naturally occurring toxins or organic warfare agents, etc. These target molecules can be detected from any source, including food samples, water samples, homogenized tissue from organisms, etc. Moreover, the biological sensor of the present invention can also be used effectively to detect multiple layers of biomolecular interactions, termed "cascade sensing." Thus, a target, once bound, becomes a probe for a secondary target. This can involve detection of small molecule recognition events that take place relatively far from the semiconductor structure's surface.

A number of strategies are available for attaching the one or more probes to the surface of the porous semiconductor structure, depending upon the type of probe which is ultimately to be attached thereto. Because of the porosity of the semiconductor structure, the probes can be bound to the exposed surfaces of the semiconductor structure throughout its central layer and its upper and lower layers.

The available strategies for attaching the one or more probes include, without limitation, covalently bonding a probe to the surface of the semiconductor structure, ionically associating the probe with the surface of the semiconductor structure, adsorbing the probe onto the surface of the semiconductor structure, or the like. Such association can also include covalently or noncovalently attaching the probe to another moiety (of a coupling agent), which in turn is covalently or non-covalently attached to the surface of the semiconductor structure.

Basically, the oxidized and hydrolyzed surface of the semiconductor structure is first functionalized (i.e., primed) with a coupling agent which is attached to the surface thereof. This is achieved by providing a coupling agent precursor and then covalently or non-covalently binding the coupling agent precursor to the surface of the semiconductor structure. Once the semiconductor surface has been primed, the probe is exposed to the primed semiconductor surface under conditions effective to (i) covalently or non-covalently bind to the coupling agent or (ii) displace the coupling agent such that the probe covalently or non-covalently binds directly to the semiconductor surface. The binding of the probe to the semiconductor structure is carried out under conditions which are effective to allow the one or more target-binding groups thereon to remain available for binding to the target molecule.

Suitable coupling agent precursors include, without limitation, silanes functionalized with an epoxide group, a thiol, or an alkenyl; and halide containing compounds.

Figure 9A:
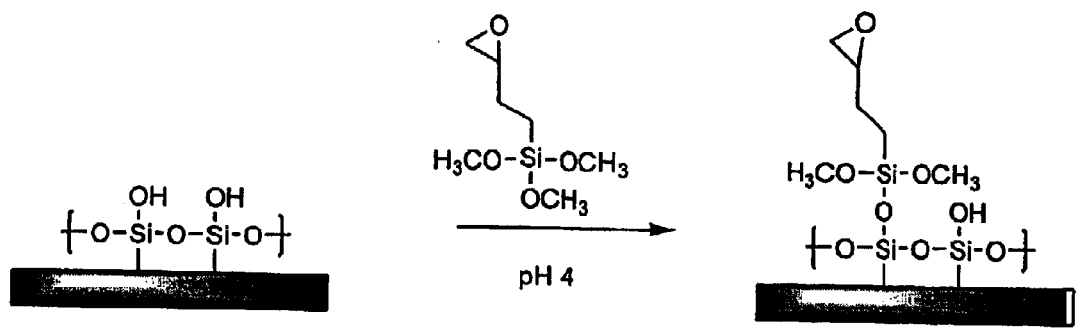
FIGS. 9A–B illustrate silanization (9A) and halide (9B) coupling agents which can be attached to a porous silicon structure and used to covalently bind probes. For purposes of illustration, trimethoxy(3-oxiranylpropyl)silane is illustrated; other silanes have been used in practice.

Silanes include a first moiety which binds to the surface of the semiconductor structure and a second moiety which binds to the probe. Preferred silanes include, without limitation, 3-glycidoxypropyltrialkoxysilanes with C1–6 alkoxy groups, trialkoxy(oxiranylalkyl)silanes with C2-12 alkyl groups and C1–6 alkoxy groups, 2-(1,2-epoxycyclohexyl)ethyltrialkoxysilane with C1–6 alkoxy groups, 3-butenyl trialkoxysilanes with C1–6 alkoxy groups, alkenyltrialkoxysilanes with C2–12 alkenyl groups and C1–6 alkoxy groups, tris[(1-methylethenyl)oxy]3-oxiranylalkyl silanes with C2–12 alkyl groups, [5-(3,3-dimethyloxiranyl)-3-methyl-2-pentenyl]trialkoxysilane with C1–6 alkoxy groups, (2,3-oxiranediyldi-2,1-ethanediyl)bis-triethoxysilane, trialkoxy[2-(3-methyloxiranyl)alkyl]silane with C1–6 alkoxy groups and C2–12 alkyl groups, trimethoxy[2-[3-(17,17,17-trifluoroheptadecyl)oxiranyl]ethyl]silane, tributoxy[3-[3-(chloromethyl)oxiranyl]-2-methylpropyl]silane, and combinations thereof. Silanes can be coupled to the semiconductor structure according to a silanization reaction scheme shown in FIG. 9A, the conditions for which are well known to those of skill in the art and described in Example 2 infra.

Figure 9B:
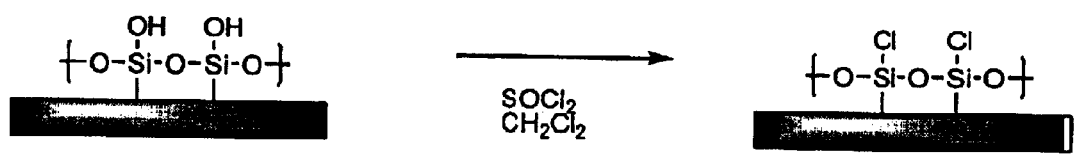

Halides can also be coupled to the semiconductor structure according to the reaction scheme set in FIG. 9B, the conditions for which are well known to those of skill in the art.

Thereafter, the one or more probes are bound to the semiconductor structure according to the type of functionality provided by the coupling agent. Typically, probes are attached to the coupling agent or displace to coupling agent for attachment to semiconductor structure in aqueous conditions or aqueous/alcohol conditions.

Figure 10A:
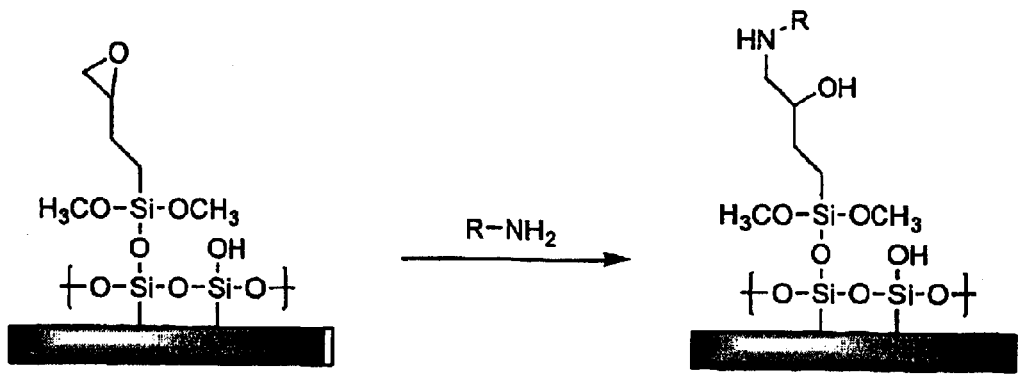
FIGS. 10A–E illustrate the attachment schemes for binding probes R-NH2, R-SH, and R-OH upon opening of the epoxide group on the coupling agent (10A–C, respectively); probe R-alkenyl to the alkenyl group on the coupling agent (10D); and probe R-OH upon displacement of a halide coupling agent (10E). For purposes of illustration, trimethoxy(3-oxiranylpropyl)silane is illustrated in FIGS. 10A–C; other silanes have been used in practice.
Figure 10B:
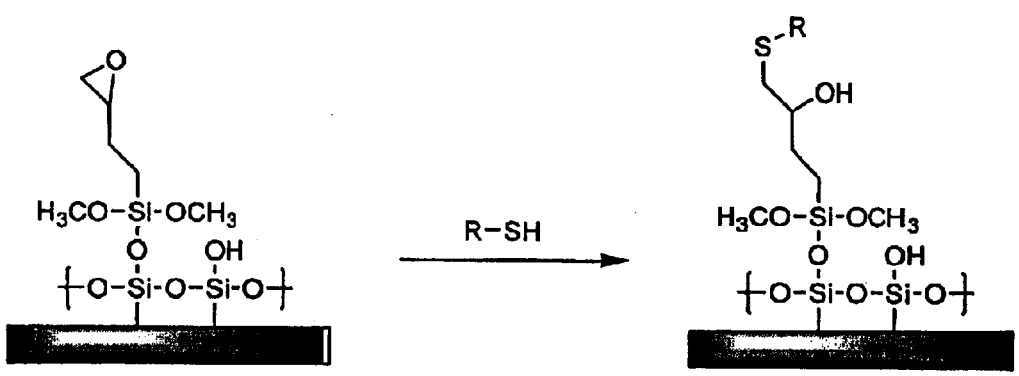
Figure 10C:
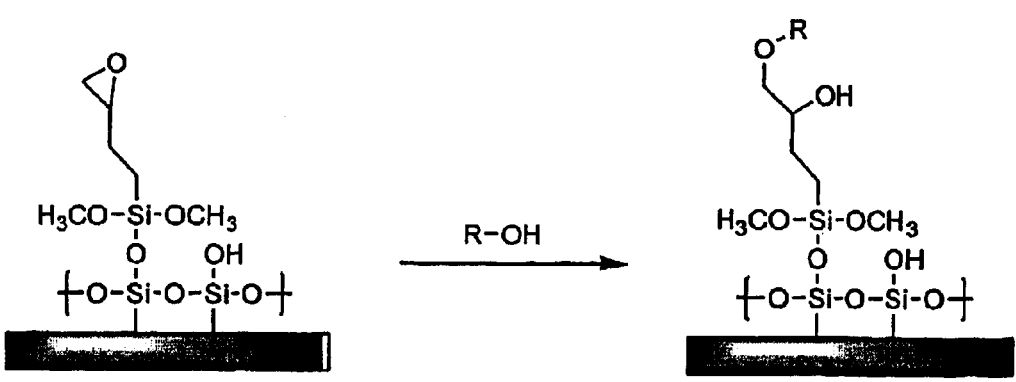

Epoxide functional groups can be opened to allow binding of amino groups according to the reaction scheme set forth in FIG. 10A, the conditions for which are well known to those of skill in the art and described in Example 3 infra. Epoxide functional groups can also be opened to allow binding of thiol groups or alcohols according to the reaction scheme set forth in FIGS. 10B–C, respectively, the conditions for which are well known to those of skill in the art.

Figure 10D:
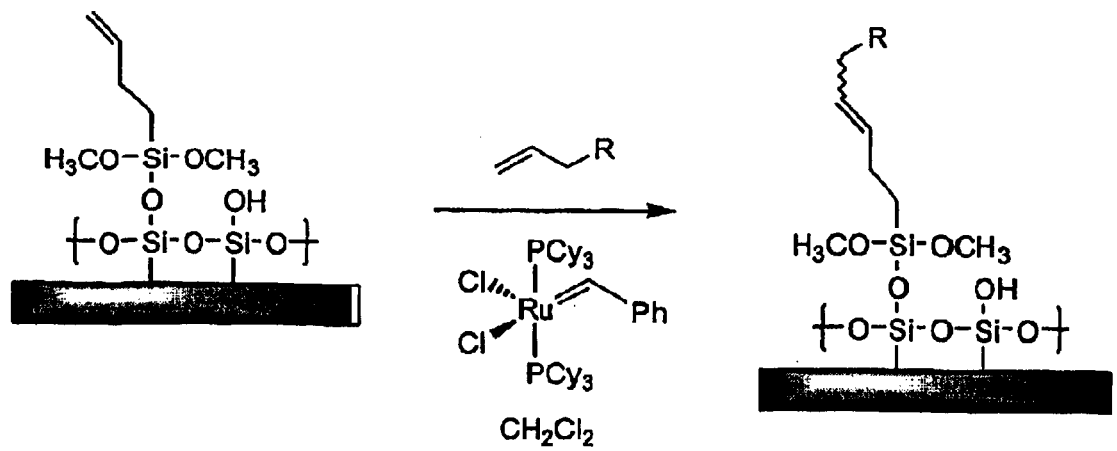
Figure 10E:
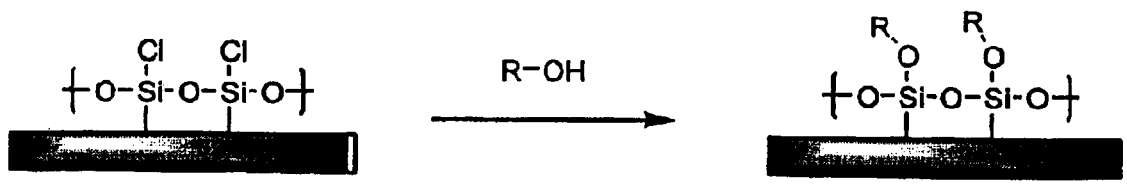

Alkenyl functional groups can be reacted to allow binding of alkenyl groups according to the reaction scheme set forth in FIG. 10D, the conditions for which are well known to those of skill in the art.

Where a halide coupling agent is employed, the halide coupling agent is typically displaced upon exposing the primed semiconductor structure to one or more probes which contain alcohol groups as the semiconductor-binding groups. The displacement can be carried out according to the reaction scheme set forth in FIG. 10E, the conditions for which are well known to those of skill in the art.

Where the one or more probes contain two or more target-binding groups, it is possible that the target-binding groups may also interact and bind to the primed surface of the semiconductor structure. To preclude this from occurring, the primed porous semiconductor structure can also be exposed to a blocking agent. The blocking agent essentially minimizes the number of sites where the one or more probes can attach to the surface of the semiconductor structure. Exposure to the blocking agent can be carried out prior to exposing the primed surface of the semiconductor structure to the probes or simultaneous therewith, although simultaneous exposure is generally preferred. The blocking agents can be structurally similar to the probes except that they lack a target-binding group or the blocking agents can simply be simple end-capping agents. By way of example, an amino acid alkyl ester (e.g., glycine methyl ester, glycine ethyl ester, 3-alanine methyl ester, etc.) blocking agent can be introduced to an epoxide-functionalized semiconductor structure surface as shown in FIG. 10A for attaching a probe to the coupling agent, except with the amino group of glycine opening the epoxide ring and covalently binding to the coupling agent.

Detectable changes in the refractive index of the biological sensor occur upon binding of the one or more probes to the target molecule will depend on the sensitivity of the type of detector employed. Many widely available detectors afford the detection of photoluminescent peak emission shifts of about 2 nm or greater.

Figure 3B:
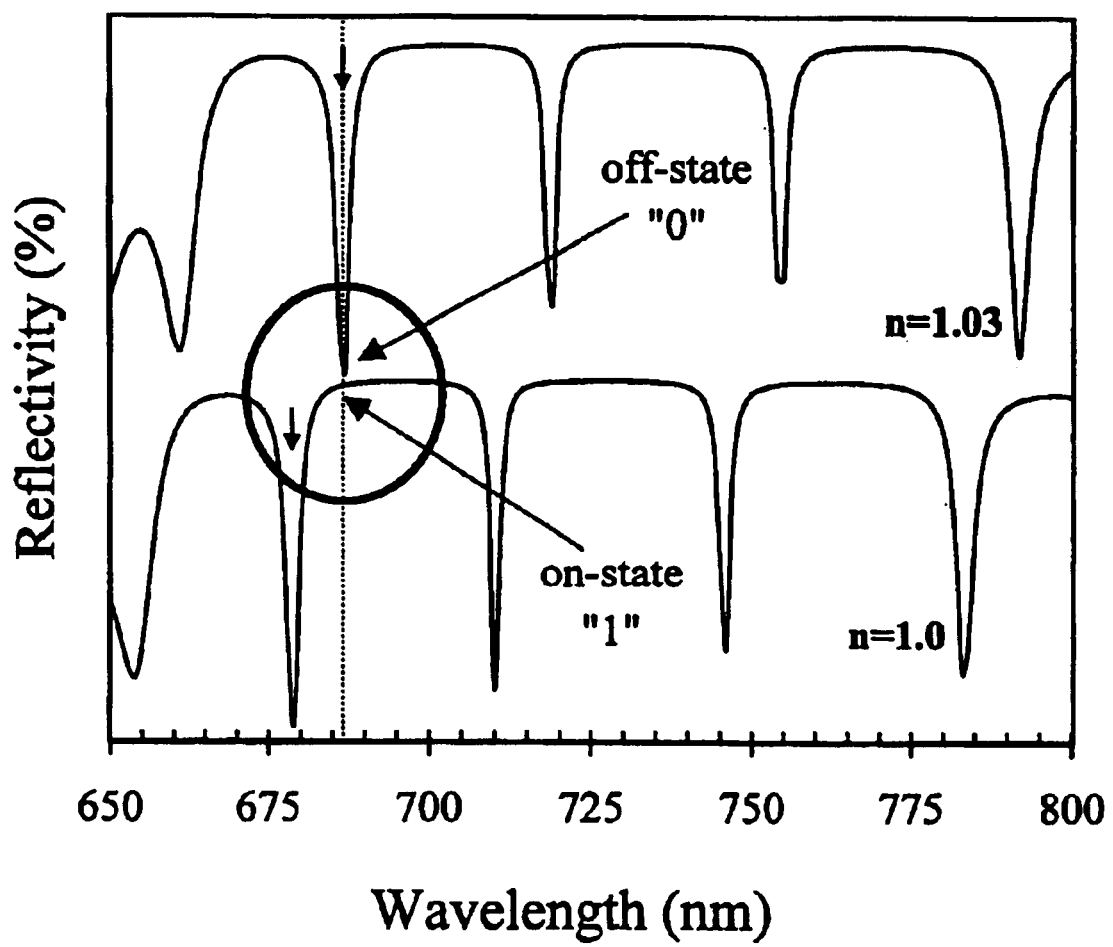

The microcavity design has an advantage over the single layer structure, in that clear "on/off" digital states exist, as shown in FIGS. 3A–B. When the refractive index (n), of the surrounding material increases from n=1.0 to n=1.03, the reflectivity spectrum red-shifts. A red-shift is predicted because the pores are filled with a material of larger refractive index. At a fixed wavelength under investigation, no "on/off" states are seen in the single layer case, shown FIG. 3A. However, for a microcavity structure shown in FIG. 3B, a distinct "on/off" state is present. At 687 nm, the digital microcavity sensor produces a "0" output signal when the refractive index of the sensing material is 1.03, and produces a "1" output signal when the refractive index changes to 1.0. This is one of the major advantages of using porous silicon based microcavity structures for sensor applications. This is particularly useful when non-quantitative detection is desired.

When quantitative detection is desired, the size of the photoluminescent peak emission shift correlates with the amount of bound target molecule which appears in the pores following exposure thereof to a sample containing the target molecule. Knowing the maximal amount of target molecule which can bind to a biological sensor of the present invention, i.e., the number of available target-binding groups on the surface-bound probes and the maximal shift which can be achieved under those conditions, it is possible to predict a quantitative concentration of the target molecule in a sample based on the detected shift which occurs.

Figure 11:
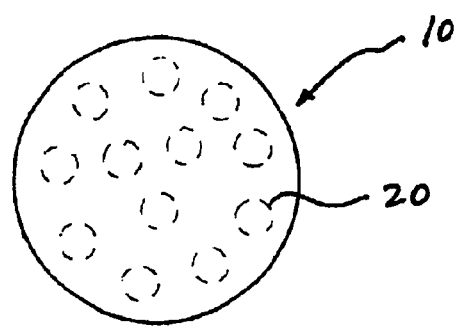
FIG. 11 illustrates schematically a microarray detector formed from a biological sensor of the present invention.

By virtue of the biological sensors of the present invention to afford a uniquely well defined luminescence shift upon binding to a target, the biological sensors can be utilized in the form of a microarray detector, schematically illustrated in FIG. 11. Thus, the microarray detector is a biological sensor 10 of the present invention which includes a number of locations or zones 20 thereon which have been functionalized to include the one or more probes. The one or more probes at each of these locations 20 can be the same (binding to the same target) or different (binding to different targets).

Figure 12:
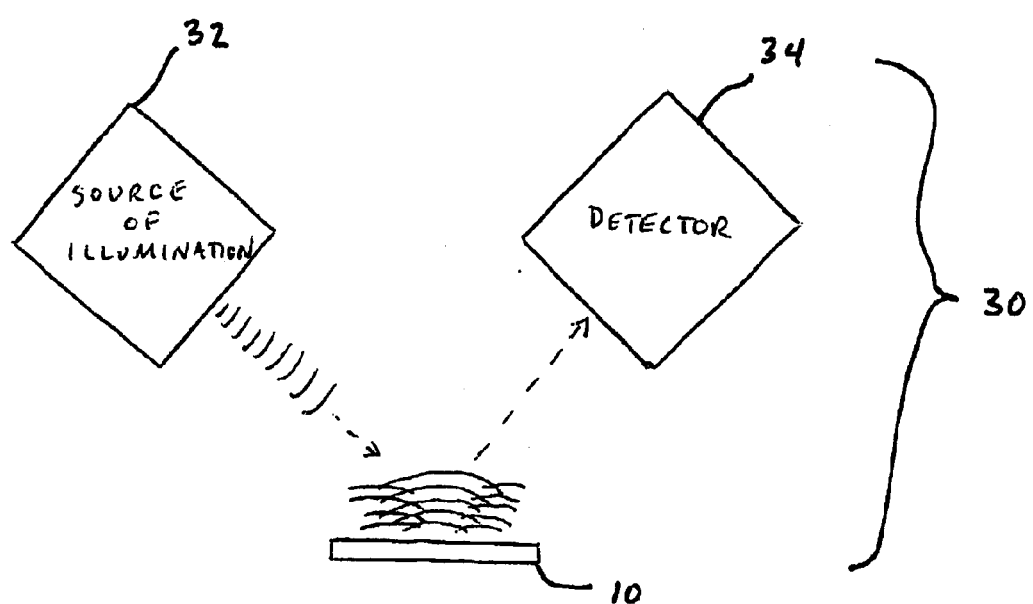
FIG. 12 illustrates schematically a detection device of the present invention which includes, as a component thereof, a biological sensor of the present invention.

As shown in FIG. 12, the biological sensor 10 of the present device is intended to be utilized as a component of a detection device 30 which also includes a source of illumination 32 (e.g., argon, cadmium, helium, or nitrogen laser and accompanying optics) positioned to illuminate the biological sensor and a detector 34 (e.g., collecting lenses, monochrometer, and detector) positioned to capture photoluminescent emissions from the biological sensor and to detect changes in photoluminescent emissions from the biological sensor. The source of illumination and the detector can both be present in a spectrometer. A computer with an appropriate microprocessor can be coupled to the detector to receive data from the spectrometer and analyze the data to compare the photoluminescence before and after exposure of the biological sensor to a target molecule.

A further aspect of the present invention relates to a method of detecting a target molecule in a sample. Basically, a biological sensor of the present invention is exposed to a sample under conditions effective to allow binding of a target molecule in the sample to the one or more probes of the biological sensor. After such exposure, it is determined whether the biological sensor emits a photoluminescent emission pattern which has shifted, indicating the presence of the target molecule in the sample.

To determine whether a shift has occurred, a first (baseline) photoluminescent emission pattern is measured prior to exposure to a sample and prior to said exposing. After exposure to the sample, a second photoluminescent emission pattern is measured and the first and second emission patterns are compared. A shift as little as about 2 nm can indicate the presence of the target in the sample. Typically, the size of the shift will depend on the size of the target to be recognized and its concentration within the sample. This determination can be performed using the detection device as described above.

As noted above, the biological sensor (and detection device containing the same) can be used to detect the presence of a pathogen in a sample. Samples which can be examined include blood, water, a suspension of solids (e.g., food particles, soil particles, etc.) in an aqueous solution, or a cell suspension from a clinical isolate (such as a tissue homogenate from a mammalian patient).

In particular, a preferred method of the present invention involves the detection of a Gram negative bacteria in a sample. This is achieved by exposing the sample to a biological sensor of the present invention which includes one or more probes that bind to lipid A or fragments thereof. A preferred probe of this type is a tetratryptophan tercyclopentane peptido-mimetic compound as disclosed in U.S. patent application Ser. No. 09/568,403 to Miller et al., filed May 10, 2000, which is hereby incorporated herein by reference in its entirety. Thereafter, a determination is made as to whether a shift in the photoluminescent emission pattern has occurred (i.e., as described above), indicating the presence of lipid A and, thus, Gram negative bacteria in sample. To ensure that any lipid A is available to bind to the probe, it is desirable but not essential to treat the sample prior to its exposure to the biological sensor in a manner effective to disrupt the cellular membrane of Gram negative bacteria in the sample, thereby releasing lipid A contained within the bacterial membrane. This can be achieved by chemical means which do not modify the structure of lipid A itself, by mechanical means (French press), by sonication, or freezing (and thawing).

Reflection of light at the top and bottom of the exemplary porous semiconductor structure results in an interference pattern that is related to the effective optical thickness of the structure. Binding of a target molecule to its corresponding probe, immobilized on the surfaces of the porous semiconductor structure, results in a change in refractive index of the structure and is detected as a corresponding shift in the interference pattern. The refractive index for the porous semiconductor structure in use is related to the index of the porous semiconductor structure and the index of the materials present (contents) in the pores. The index of refraction of the contents of the pores changes when the concentration of target species in the pores changes. Most commonly, the target is an organic species that has a refractive index that is larger than that of the semiconductor structure. The replacement of a species of lower index of refraction (air or other vapor medium) by another species of higher index of refraction (target species) would be expected to lead to an increase in the overall value for index of refraction. An increase in index should result in a shift in the interference pattern wavelengths to longer values; i.e., a bathochromic or "red" shift.

From all of the above, it should be appreciated that the biological sensor can be used with appropriate probes for purposes of defining protein—protein interactions for proteomics, defining molecular interaction partners involved in the regulation of gene transcription events, for genomic analysis, for metabonomic analysis, and in general for screening drugs to determine their interactions with particular proteins or nucleic acids, as well as for screening combinatorial libraries which bind to a particular probe (which itself can be a biochemical target for therapeutic or preventative treatments).

EXAMPLES

The following examples are intended to illustrate, but by no means are intended to limit, the scope of the present invention as set forth in the appended claims.

Example 1

Synthesis of Porous Silicon Microcavity

Porous silicon samples are produced electrochemically with computer control. This allows precise control of the current density and switching times necessary in the fabrication of multilayer structures and assures maximum reproducibility.

The multilayer structure is created using a periodic current density square pulse during the electrochemical dissolution process. The dissolution of the silicon atoms is mainly restricted to a region next to the substrate, therefore the porous layer first formed remains intact throughout subsequent etching. By varying the current density during the etch, it is possible to change the porosity at the silicon/electrolyte interface.

Porous silicon multilayer mirrors and microcavity resonators are electrochemically formed by anodic etching in a hydrofluoric electrolyte. Table 1 below details the experimental conditions used in the formation of porous silicon 10 multilayer mirrors.

TABLE 1

Porous Silicon Multilayer Structures: Anodization Conditions

| | |
|---|---|
| Substrate resistivity (Ω-cm) | P⁺(0.008–0.012) |
| Electrolyte | 15% HF |
| Regeneration time (sec/layer) | 2 |
| Periods | 6–10 |
| $J_1$ (mA/cm$^2$) | 5 |
| $t_1$ (sec) | 20 |
| Porosity$_1$ (%) | 43 |
| Thickness$_1$ (nm) | 80 |
| $J_2$ (mA/cm$^2$) | 30 |
| $t_2$ (sec) | 10 |
| Porosity$_2$ (%) | 62 |
| Thickness$_2$ (nm) | 160 |

A 2 sec per layer regeneration time at zero current is incorporated into the formation scheme to allow the system to reach equilibrium before the formation of another porous silicon layer. The dissolution of silicon atoms is restricted by the carrier transport in the porous silicon structure itself and by the mass transport of the reactants through the pores. It follows Fick's law:

$$F_{HF} = D_{HF} \frac{c_{top} - c_{bot}}{d}$$

where $F_{HF}$ is the flux of the HF molecules, $D_{HF}$ the diffusion coefficient of these molecules into the pores, $c_{top}$ and $c_{bot}$ the HF concentrations at the top and the bottom of the porous silicon layer, respectively, and d the layer thickness. During regeneration time, the HF concentration at the bottom can recover and the overall depth homogeneity of the layer can be improved. This allows the HF concentration in the electrolyte to return to its original level, which allows the fabrication of stable multilayer structures. The porosity values are estimated using a porosity dependence on current density plot for various concentrations of HF. Thickness values were obtained through scanning electron microscopy (SEM). The microcavity resonator contains an additional porous silicon layer embedded between two anti-symmetric multilayer mirrors.

Two types of microcavity resonators are formed: single peak microcavity resonators and multiple peak microcavity resonators. A single peak microcavity resonator contains a highly luminescent active layer with a large porosity (>75%) and is approximately 200 nm thick. The current density used for its formation varies from 80–150 mA/cm$^2$ (depending on the desired active layer porosity) for an etching time between 1–20 seconds. The multiple peak microcavity resonator has an active layer that is completely opposite from a single peak microcavity resonator. The multiple peak microcavity contains a lower porosity (<70%) active layer which is relative thick (>1 μm). The current density used ranges from 10–40 mA/cm$^2$ for etching times of 200–600 seconds.

After anodization, the porous silicon samples are thermally oxidized in a flowing dilute oxygen environment at 900° C. for 10 minutes. This provided an oxide surface that was subsequently used for the immobilization chemistry in the fabrication of the biosensor.

Pore sizes of different types of porous silicon can vary from nanometers to microns. Anodization of a p⁺ (0.01 ω-cm) substrate creates a mesoporous layer, where the pore size ranges from 10 to 100 nm (Theiβ, "Optical Properties of Porous Silicon," *Surface Science Reports*, 29:91–192 (1997), which is hereby incorporated by reference in its entirety). The pores are elongated along the crystalline plane of the silicon structure and resemble a network of silicon wires. In all nanosilicon sensor structures described herein this paper, the oxidized porous silicon multilayer stack contained alternating layers of low porosity (43%) and high porosity (62%), with thicknesses of 80 nm and 160 nm, respectively. The columnar pore structure of the active layer in the microcavity resonator has pore diameters between 50 nm–75 nm. The pore diameter is a crucial factor in the fabrication of a biosensor because the pores must be large enough to allow penetration and attachment of the sensing molecules.

Example 2

Preparation of DNA Binding Sensor

Using a porous silicon microcavity structure prepared according to Example 1, a DNA binding sensor was prepared by attaching a DNA probe to the porous silicon microcavity.

Silanization of the porous silicon microcavity was achieved by its incubation in a 5% solution of 3-glycidoxypropyl trimethoxy silane in water/ethanol (1:1) for 14 hours. Silane solution was then drained off, and the silanized device washing repeatedly with glass-distilled, deionized water.

The silanized porous silicon microcavity structures were exposed to a 24-mer DNA molecule according to SEQ ID No: I as follows:
tagctatgga attcctcgta ggca 24
The 24-mer DNA molecules covalently bond to the silanized surface, where they become immobilized. The nucleophilic amine group, attached at the 3' end of the DNA strand, attacks the epoxide ring of the silane. The porous silicon—DNA samples are initially placed in a constant temperature water bath where they are incubated at 37° C. for approximately 20 hours. The DNA attached samples are then rinsed in double distilled water to remove unbound DNA and dried under a stream of nitrogen.

It is important to note that throughout the processing steps, i.e. silanization and attachment of DNA, the microcavity structure remains intact and undamaged (Vo-Dinh et al., *Anal. Chem.* 71:358–363 (1999); Chan et al., *Phys. Stat. Sol. A,* 182:541–546 (2000), each of which is hereby incorporated by reference in its entirety).

Example 3

Binding Complementary DNA with DNA Binding Sensor

A DNA binding sensor of Example 2 was used to bind a strand of DNA complementary to the probe. The complementary 22-mer DNA molecule has a nucleotide sequence according to SEQ ID No: 2 as follows:
gcctacgagg aattccatag ct 22
The sensing probes of single stranded DNA molecules seek out only their complement in a complex mixture of DNA containing a large number of other nucleic acid molecules. Binding is allowed to proceed for 1 hour at room temperature in aqueous solution. Binding of the complementary DNA molecule was confirmed using Fourier Transform Infrared Spectroscopy.

Figure 4A:
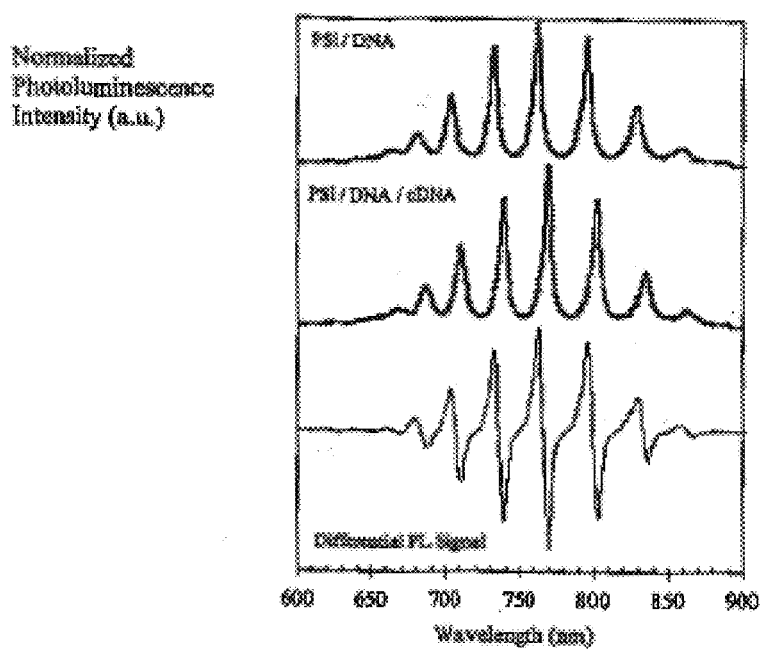
FIGS. 4A–B illustrate the effects of DNA—DNA hybridization on a DNA binding sensor of the present invention. 50 μM of DNA is attached to the porous silicon microcavity structure, whose luminescence spectrum is shown at the top of FIG. 4A. 1 μM of complementary DNA is exposed to the DNA attached porous silicon and a 7 nm red-shift is observed after binding (middle spectrum of FIG. 4A). A large differential photoluminescence signal is obtained by taking the difference between the two spectra (bottom spectrum of FIG. 4A). When a non-complementary strand of DNA is exposed to the porous silicon sensor, no shifting of the luminescence peaks is observed, and the differential signal is negligible.
Figure 4B:
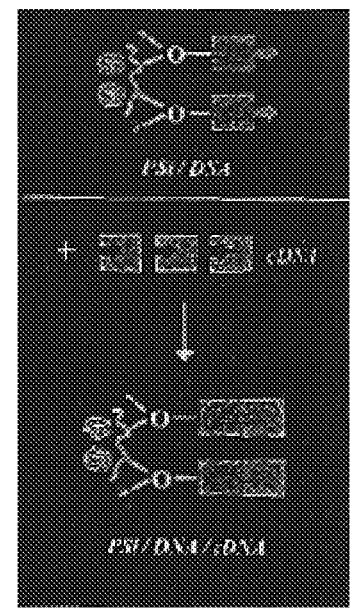

The effect of DNA—cDNA binding is exemplified in FIG. 4A. By taking the difference between the photoluminescence spectra before and after DNA-cDNA hybridization, a 7 nm red-shift is observed, suggesting that the change in refractive index increased by 0.03. This change is best noted as a change in optical thickness, since a slight increase in thickness also induces a red-shift.

To ensure the presence and immobilization of DNA in the porous silicon layer, a fluorescent probe molecule is attached to the target DNA. The fluorescence occurs at ~550 nm, which does not interfere with the luminescence of porous silicon at the 700–850 nm region. A large increase in the integrated area of fluorescence is observed when a 10 μM concentration of DNA-attached porous silicon is exposed to 1 μM of target cDNA. This suggests that most of the target cDNA molecules binded to the immobilized probe DNA in the porous matrix. Also, as the concentration of probe DNA increases, the amount of target cDNA immobilized on porous silicon also increases. This is confirmed by a steady increase in the integrated area of the fluorescence.

Another method to confirm DNA attachment is through radioactive labeling. Radioactive labeling has the advantage of providing a more quantitative analysis to DNA attachment that complements the qualitative results obtained from fluorescent tagging. Once the probe DNA has been successfully labeled, it is then attached (i.e., allowed to hybridize) to the silanized surface of porous silicon. Results indicate that under constant silanization conditions (0.5% aqueous silane solution), approximately 30% of the exposed DNA is attached to the porous matrix.

Example 4

Effects of Desiccation on DNA Binding Sensor

During the course of experiments, temporary storage of the DNA immobilized porous silicon samples often is required. Various storage options were investigated: dry in a dessicator, dry in ambient, and wet in ambient, all stored at room temperature. Storage is important because any degradation to the immobilized DNA will yield inaccurate results.

Figure 5:
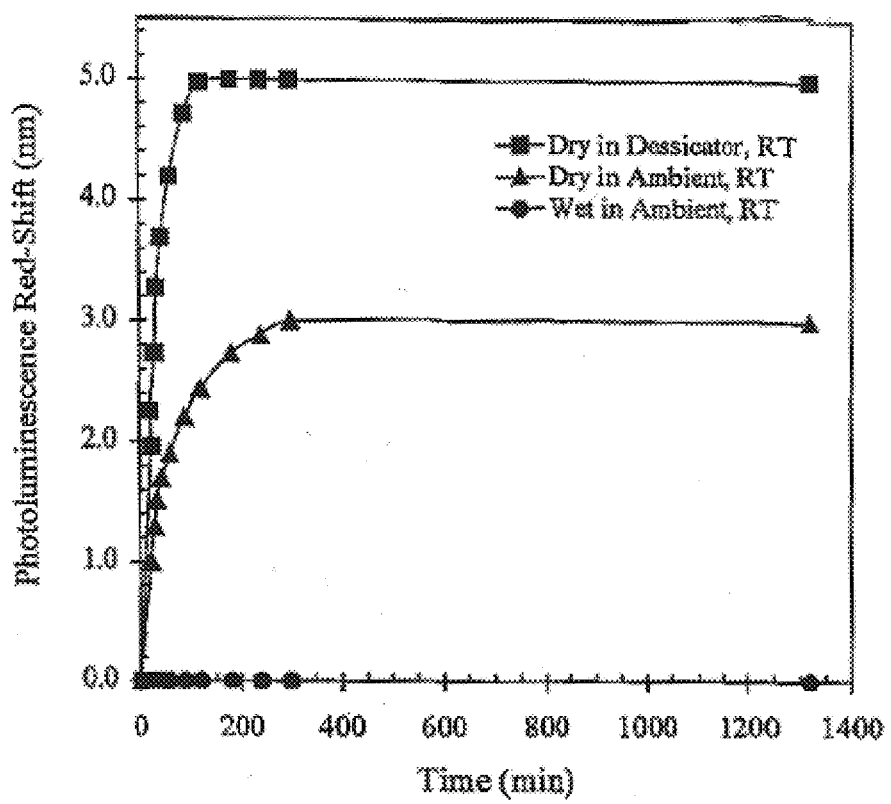
FIG. 5 illustrates the stability of the immobilized DNA biosensor is investigated under three different storage conditions at room temperature: dry in a desiccator, dry in ambient air, and covered with water. Results show that storage conditions in a desiccator result in the largest photoluminescence peak red-shift of 5 nm in 3 hours. A 3 nm red-shift is observed for the sensor stored under ambient conditions for 5 hours, while the most stable storage condition of the DNA sensor is covered with water.

For the sample stored dry in a dessicator, a moderate photoluminescence red-shift of 5 nm is observed after 3 hours. A slower response is observed for the sample stored dry in ambient air, where a 3 nm photoluminescence red-shift is detected after 5 hours of storage. However, the most stable samples are the DNA immobilized biochips covered with water at room temperature. For this scenario, no detectable shifts in the photoluminescence spectra are observed for up to 22 hours of testing. Results of these control experiments are graphically shown in FIG. 5.

Example 5

Preparation of Viral Biosensor

A DNA biosensor suitable for detecting full length viral DNA was prepared substantially as described in Example 2, except that a 30-mer DNA molecule was used as a probe. The 30-mer probe has a nucleotide sequence according to SEQ ID No: 3 as follows:
tcggagagcc ttggtgttca atatcatcat 30
Lambda is a double stranded DNA bacteriophage of *Escherichia coli.* (or *E. coli.*). There are 48,502 base pairs in the entire DNA sequence of bacteriophage lambda with a total molecular weight of $31.5 \times 10^6$ Daltons (A. D. Hershey, *The Bacteriophage Lambda* The Cold Spring Harbor Laboratory, New York, USA (1971), which is hereby incorporated by reference in its entirety). The base pairing strength of the 30 nucleotide DNA is strong enough to bind to the extremely large DNA of bacteriophage lambda. One issue of concern in working with large DNA oligonucleotides is the degree of folding that may occur within the molecule. Although this is a concern when considering which segment of the bacteriophage lambda the complementary DNA will bind to, it is important to note that the forces between base pairs are much stronger than the folding forces.

The probe was ordered from a commercial synthesis lab and 50 μM thereof was immobilized in the silanized porous silicon matrix in accordance with the procedures described in Example 2.

To test the recognition and binding of bacteriophage lambda, 194.2 fM of the lambda DNA was exposed to the porous chip. The chip was placed in a water bath and heated to 89° C. (denaturation temperature of bacteriophage lambda DNA) for 3 minutes, and then incubated at 37° C. for one hour. At 89° C., the double stranded DNA of bacteriophage lambda separates into two individual strands. When the temperature is reduced to 37° C., one of the separated DNA strands finds and attaches to the 30-mer complementary DNA immobilized on the chip. However, the two separated strands of DNA can also recombine. To increase the probability that the viral DNA has the opportunity to bind to the immobilized complementary DNA, excess amounts of the 30 nucleotide segmented complementary DNA are immobilized onto the chip. After hybridization, the chip is thoroughly rinsed with double distilled water to rinse away all residual DNA that is not covalently bonded to the porous matrix.

Figure 6:
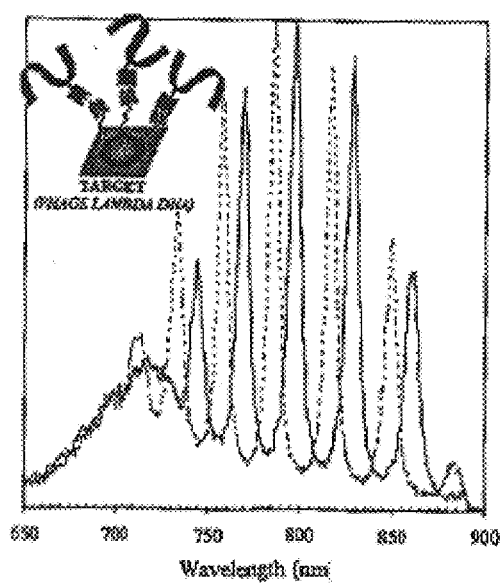
FIG. 6 illustrates the room temperature photoluminescence spectra taken before (dotted line) and after (solid line) recognition and binding of bacteriophage lambda to a 30-mer nucleotide complementary DNA sequence immobilized in a porous silicon microcavity structure. A 12 nm red-shift was observed for sensing bacteriophage lambda at concentration of 194.2 fM. The inset picture schematically depicts the porous silicon sensor binding a complete strand of the lambda DNA (48,502 base pairs) to a short probe strand of complementary DNA.

The recognition and binding of bacteriophage lambda to a partial cDNA sequence immobilized in the porous matrix was confirmed through photoluminescence spectral shifts. FIG. 6 shows a 12 nm red-shift in the photoluminescence peaks, induced by a change in the effective refractive index of the material upon coupling of the nucleotides. A relatively large red-shift is observed because the sensing virus is much larger than the previous experiments of the short oligonucleotide DNA biosensor (bacteriophage lambda has 48,502 base pairs, compared to the 24 base pairs of the DNA biosensor tested in Example 3).

A series of control experiments was also performed to confirm viral DNA hybridization. When a partial cDNA immobilized biochip was exposed to a buffer solution without any bacteriophage lambda DNA, no shifts in the photoluminescence spectra were detected. This established two experimental facts: the buffer solution does not change the effective refractive index of the system, and subsequent temperature treatments (denaturation of the bacteriophage lambda DNA at 89° C.) do not induce any shifting in the photoluminescence spectra. This confirms the validity of recognition and binding of the bacteriophage lambda DNA to its segmented cDNA sequence.

Example 6

Preparation of Gram Negative Bacterial Biosensor

To specifically detect Gram-(−) bacteria, it was first necessary to select a target molecule present to a significantly greater extent in this bacterial subclass than in Gram-(+) bacteria. Lipopolysaccharide (LPS) is a primary constituent of the outer cellular membrane of Gram-(−) bacteria (Young et al., *Ann. Intern. Med.* 86:456–471 (1977), which is hereby incorporated by reference in its entirety) and is commonly known as bacterial endotoxin, the causative agent of sepsis (Raetz, *Ann. Rev. Biochem.* 59:129–170 (1990), which is hereby incorporated by reference in its entirety). The precise structure of LPS varies among bacterial species, but is overall composed of three parts: a variable polysaccharide chain, a core sugar, and lipid A. As lipid A is highly conserved among LPS subtypes, this seemed a natural target. An organic receptor, tetratryptophan ter-cyclo pentane, designated TWTCP, was designed and synthesized which specifically binds to diphosphoryl lipid A in water with a dissociation constant of 592 nM (Hubbard et al., *J. Am. Chem. Soc.* 123:5811–5812 (2001), which is hereby incorporated by reference in its entirety).

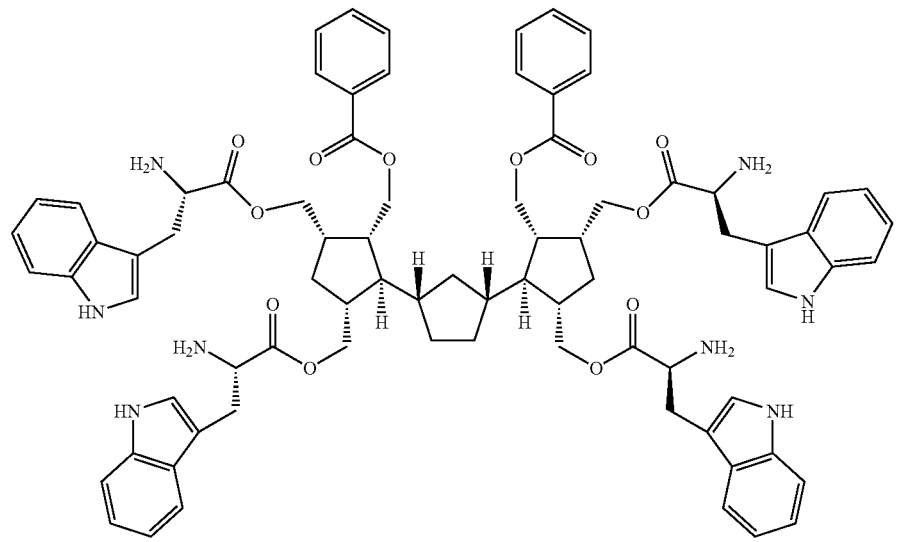

TWTCP

To provide functionality capable of forming a stable bond between the organic probe molecule TWTCP and the inorganic silicon surface, the device was first treated with an aqueous solution of 3-glycidoxypropyltrimethoxy silane. Silanization of the device was achieved by its incubation in a 5% solution of 3-glycidoxypropyl trimethoxysilane in water/ethanol (1:1) for 14 hours. Silane solution was then drained off, and the silanized device washing repeatedly with glass-distilled, deionized water.

To prevent all four amino groups of the tetratryptophan receptor from reacting with the functionalized porous silicon surface, thus blocking access to the binding face of the receptor molecule, a blocking agent was used. Basically, 200 µl of an aqueous solution consisting of TWTCP:glycine methyl ester at various ratios (total concentration 750 µl, 0.6% DMSO) was exposed to the chip at ambient temperature in a wetting chamber overnight. The chip was then rinsed repeatedly with glass-distilled, deionized water, and dried under a stream of nitrogen.

Figure 7:
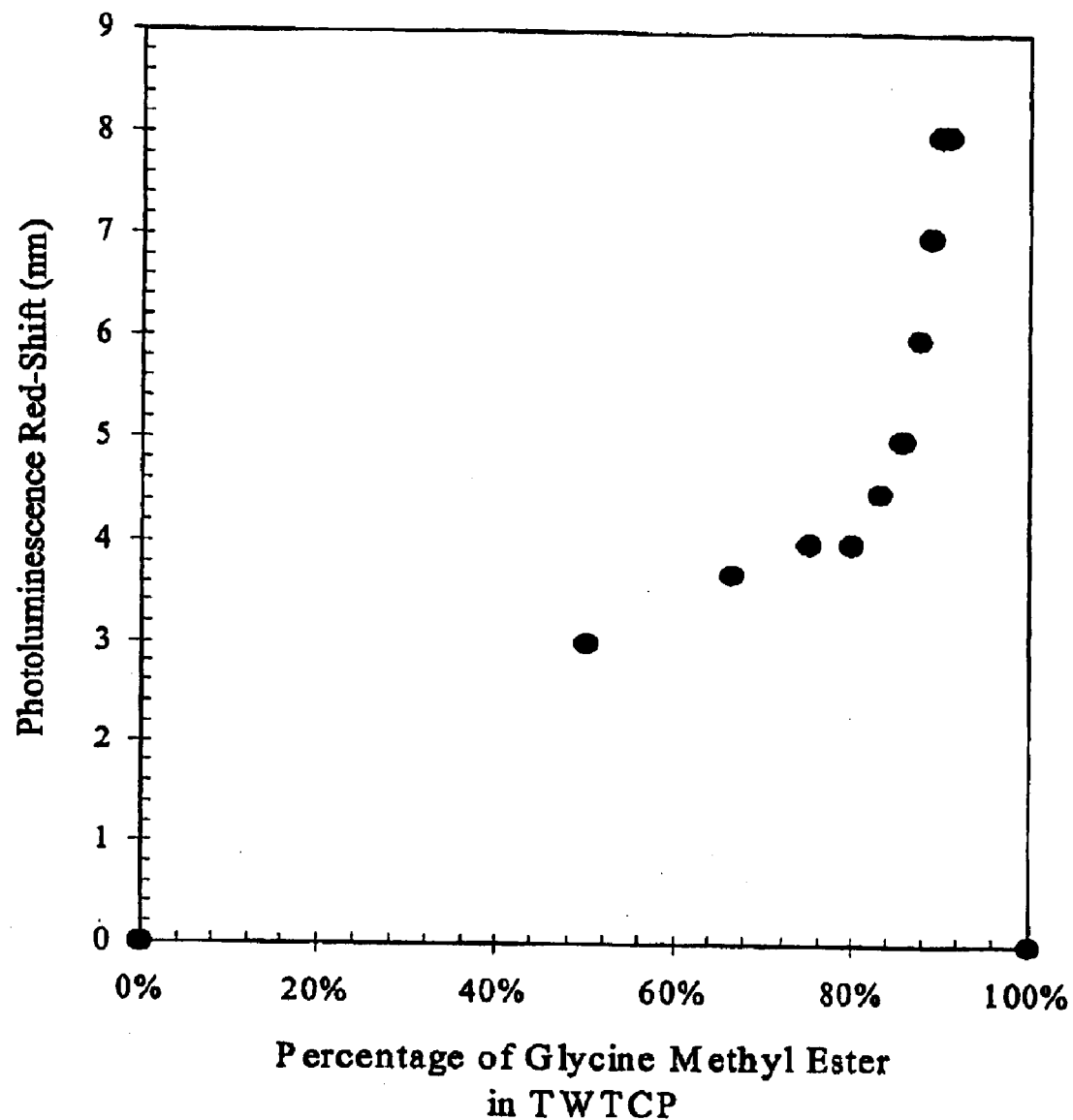
FIG. 7 is a graph illustrating the response of functionalized porous silicon microcavities to lipid A as a function of TWTCP:glycine methyl ester ratio.

Using glycine methyl ester as the blocking agent and examining the response of the sensor to purified lipid A, it was discovered that the optimal ratio of receptor to blocker molecules was about 1:10 (TWTCP: glycine methyl ester) (FIG. 7). In this case, incubation of the sensor with a solution of lipid A produces an 8 nm red-shift in the photoluminescence peak wavelength. When a 100% solution of TWTCP, or a 100% solution of glycine methyl ester is immobilized in the porous matrix, no shifting of the luminescence peaks is detected after exposure to lipid A.

Because porous silicon is a complex three-dimensional material, a precise determination of the amount of receptor (TWTCP) immobilized on each device, as well as the proportion of the interior surface area covered, is not straightforward. Using radiolabeled oligonucleotides, it was determined that a porous silicon microcavity, prepared and silanized with 3-glycidoxypropyl trimethoxy silane under identical conditions to those described above, covalently bound 20% of 200 µl of a 50 µM solution, or 2 nmol of DNA. Assuming the same number of reactive sites, and given the 1:10 dilution of TWTCP:glycing methyl ester employed in the experiment, this result would suggest that approximately 0.2 nmol of TWTCP is immobilized on each chip.

Example 7

Detection of Gram Negative Bacteria

To determine the ability of the sensor prepared in Example 6 to differentiate between two classes of bacteria, independent overnight cultures of Gram-(−) bacteria (*E. coli*) and Gram-(+) bacteria (*Bacillus subtilis*) were grown up, centrifuged, and then individually lysed following resuspension in phosphate buffer solution (PBS, pH 7.4). Upon exposure of the lysed Gram-(−) cells to the sensor, a 4 nm photoluminescence red-shift was detected, shown as the right spectra of FIG. 8. (It was observed that the minimum time it takes to red-shift the photoluminescence peaks by 4 nm is about one hour, with prolonged time exposures of up to 5 hours showing no additional shift.) However, when the microcavity sensor was exposed to a solution of lysed Gram-(+) bacteria, no shifting of the luminescence peaks was observed, depicted by the left spectra of FIG. 3. It is believed the large shift is attributable to the recognition and binding of the TWTCP receptor with the lipid A present in the bacterial cell wall. Analogous results were obtained with several other species of Gram-(+) and Gram-(−) bacteria as shown in Table 2 below.

TABLE 2

Photoluminescent Detection of Gram Negative or Positive Bacteria

| Bacterium | Class | Photoluminescent red-shift |
|---|---|---|
| *Escherichia coli* | Gram-(−) | 4 nm |
| *Bacillus subtilis* | Gram-(+) | none detected |
| *Lactobacillus acidiophilus* | Gram-(+) | none detected |
| Salmonella spp. | Gram-(−) | 3 nm |
| *Pseudomonas aeruginosa* | Gram-(−) | 3 nm |

These results demonstrate the ability of a porous silicon microcavity biosensor to distinguish between Gram-(−) and Gram-(+) bacteria. Clear modulation of the photoluminescence spectra from microcavity device structures illustrates their application as biosensors that can translate the recognition of lipid A present in bacterial cell walls into an optical signal. The remarkable features of these silicon sensors (integratable, high surface-to-volume ratio, robust, inexpensive, small, ease of use) should allow arrays to be constructed to simultaneously identify a variety of analytes by simply functionalizing the surface with arrays of specific, high-affinity receptor molecules.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:

1. A biological sensor comprising:
   a porous semiconductor structure comprising a central layer interposed between upper and lower layers, each of the upper and lower layers including strata of alternating porosity, and the central layer having a porosity of about 50 about 90 percent; and
   one or more probes coupled to the porous semiconductor structure, the one or more probes being able to bind to a target molecule, whereby a detectable change occurs in a refractive index of the biological sensor upon binding of the one or more probes to the target molecule.

2. The biological sensor according to claim 1 wherein the central active layer has a porosity of about 65 to about 85 percent.

3. The biological sensor according to claim 1 wherein each of the upper and lower layers comprise six or more strata of alternating porosity.

4. The biological sensor according to claim 1 wherein the strata of alternating porosity comprise first stratum having a porosity of about 35 to about 70 percent and second stratum having a porosity greater than the porosity of the first stratum.

5. The biological sensor according to claim 1 wherein the porous semiconductor structure comprises pores with an average pore size of between about 2 nm to about 2000 nm.

6. The biological sensor according to claim 1 wherein the porous semiconductor structure comprises pores with an average pore size of between about 10 nm to about 100 nm.

7. The biological sensor according to claim 1 wherein the probe is a non-polymeric small molecule selected from the group consisting of avidin, peptido-mimetic compounds, and vancomycin.

8. The biological sensor according to claim 1 wherein the probe is a tetratryptophan ter-cyclopentane which binds to lipopolysaccharide.

9. The biological sensor according to claim 1 wherein the probe is a polypeptide selected from the group consisting of a receptor for cell surface molecule, a lipid A receptor, an antibody or fragment thereof, a peptide monobody, a lipopolysaccharide-binding polypeptide, a peptidoglycan-binding polypeptide, a carbohydrate-binding polypeptide, a phosphate-binding polypeptide, a nucleic acid-binding polypeptide, and a polypeptide which binds an organic warfare agent.

10. The biological sensor according to claim 1 wherein the probe is a nucleic acid molecule.

11. The biological sensor according to claim 1 further comprising:
    one or more coupling agents each comprising a first moiety attached to the porous semiconductor structure and a second moiety which binds to the probe.

12. The biological sensor according to claim 11 wherein the one or more coupling agents are silanes.

13. The biological sensor according to claim 12 wherein the silanes are selected from the group consisting of 3-glycidoxypropyltrialkoxysilanes with C1–6 alkoxy groups, trialkoxy(oxiranylalkyl)silanes with C2–12 alkyl groups and C1–6 alkoxy groups, 2-(1,2-epoxycyclohexyl)ethyltrialkoxysilane with C1–6 alkoxy groups, 3-butenyl trialkoxysilanes with C1–6 alkoxy groups, alkenyltrialkoxysilanes with C2–12 alkenyl groups and C1–6 alkoxy groups, tris[(1-methylethenyl)oxy]3-oxiranylalkyl silanes with C2–12 alkyl groups, [5-(3,3-dimethyloxiranyl)-3-methyl-2-pentenyl]trialkoxysilane with C1–6 alkoxy groups, (2,3-oxiranediyldi-2,1-ethanediyl)bis-triethoxysilane, trialkoxy[2-(3-methyloxiranyl)alkyl]silane with C1–6 alkoxy groups and C2–12 alkyl groups, trimethoxy[2-[3-(17,17,17-trifluoroheptadecyl)oxiranyl]ethyl]silane, tributoxy[3-[3-(chloromethyl)oxiranyl]-2-methylpropyl]silane, and combinations thereof.

14. The biological sensor according to claim 11 wherein each of the one or more probes comprises a plurality of binding sites, at least one of which binds to the target and at least one of which is bonded to the second moiety of the coupling agent.

15. The biological sensor according to claim 14 wherein the plurality of binding sites on the probe are the same, the biological sensor further comprising:
    a plurality of blocking agents, each bonded to the second moiety of the coupling agent under conditions effective to preclude all of the plurality of binding sites on a single probe from binding to the second moieties on the one or more coupling agents.

16. The biological sensor according to claim 15 wherein the plurality of blocking agents are amino acid alkyl esters.

17. The biological sensor according to claim 1 wherein the one or more probes are the same.

18. The biological sensor according to claim 1 wherein the one or more probes are coupled to the porous semiconductor structure throughout the central layer and the upper and lower layers.

19. The biological sensor according to claim 1 wherein the one or more probes comprises two or more probes which are different, each binding to different target molecules.

20. The biological sensor according to claim 19 wherein the porous semiconductor structure includes at least two zones, one of the two or more probes being bonded to the porous semiconductor structure within a first zone and another of the two or more probes being bonded to the porous semiconductor structure within a second zone.

21. The biological sensor according to claim 1 wherein the central layer is a microcavity and each of the upper and lower layers is a Bragg reflector.

22. The biological sensor according to claim 1 wherein strata of alternating porosity comprise strata of alternating higher and lower relative porosity.

23. A detection device comprising:
    a biological sensor according to claim 1;
    a source of illumination positioned to illuminate the biological sensor; and a detector positioned to capture photoluminescent emissions from the biological sensor and to detect changes in photoluminescent emissions from the biological sensor.

24. A method of detecting a target molecule comprising:

exposing a biological sensor according to claim 1 to a sample under conditions effective to allow binding of a target molecule in the sample to the one or more probes of the biological sensor; and determining whether the biological sensor emits a photoluminescent emission pattern which shifts following said exposing, whereby a shifted photoluminescent emission pattern indicates the presence of the target molecule in the sample.

25. The method according to claim 24 wherein said determining comprises:

measuring a first photoluminescent emission pattern prior to said exposing;

measuring a second photoluminescent emission pattern after said exposing; and comparing the first and second photoluminescent emission patterns.

26. The method according to claim 24 wherein said measuring is carried out using a light source and a spectral analyzer.

27. The method according to claim 24 wherein the target molecule is a protein, glycoprotein, peptidoglycan, carbohydrate, lipoprotein, lipoteichoic acid, lipid A, phosphate, nucleic acid, or organic compound.

28. A method of detecting the presence of Gram negative bacteria in a sample comprising:

exposing a sample to a biological sensor according to claim 1 wherein the one or more probes bind to lipid A or fragments thereof; and determining whether the biological sensor emits a photoluminescent emission pattern which shifts following said exposing, whereby a shifted photoluminescent emission pattern indicates the presence of lipid A and, thus, Gram negative bacteria in the sample.

29. A biological sensor comprising:

a porous semiconductor structure comprising a central layer interposed between upper and lower layers, each of the upper and lower layers including six or more strata of alternating porosity; and one or more probes coupled to the porous semiconductor structure, the one or more probes being able to bind to a target molecule, whereby a detectable change occurs in a refractive index of the biological sensor upon binding of the one or more probes to the target molecule.

30. A detection device comprising:

a biological sensor according to claim 29;

a source of illumination positioned to illuminate the biological sensor; and a detector positioned to capture photoluminescent emissions from the biological sensor and to detect changes in photoluminescent emissions from the biological sensor.

31. A method of detecting a target molecule comprising:

exposing a biological sensor according to claim 29 to a sample under conditions effective to allow binding of a target molecule in the sample to the one or more probes of the biological sensor; and determining whether the biological sensor emits a photoluminescent emission pattern which shifts following said exposed, whereby a shifted photoluminescent emission pattern indicates the presence of the target molecule in the sample.

32. A biological sensor comprising:

a porous semiconductor structure comprising a central layer interposed between upper and lower layers, each of the upper and lower layers including strata of alternating porosity; and one or more probes coupled to the porous semiconductor structure throughout the central layer and the upper and lower layers, the one or more probes being able to bind to a target molecule, whereby a detectable change occours in a refractive index of the biological sensor upon binding of the one or more probes to the target molecule.

33. A detection device comprising:

a biological sensor according to claim 32;

a source of illumination positioned to illuminate the biological sensor; and a detector positioned to capture photoluminescent emissions from the biological sensor.

34. A method of detecting a target molecule comprising:

exposing a biological sensor according to claim 32 to a sample under conditions effective to allow binding of a target molecule in the sample to the one or more probes of the biological sensor; and determining whether the biological sensor emits a photoluminescent emission pattern which shifts following said exposing, whereby a shifted photoluminescent emission pattern indicates the presence of the target molecule in the sample.

* * * * *